(12) United States Patent
Vetter

(10) Patent No.: US 6,447,610 B1
(45) Date of Patent: Sep. 10, 2002

(54) COATING INSIDE OF SYRINGE

(75) Inventor: Udo J. Vetter, Ravensburg (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 09/618,442

(22) Filed: Jul. 18, 2000

(30) Foreign Application Priority Data

Jul. 24, 1999 (DE) .......................................... 199 34 841

(51) Int. Cl.⁷ .............................. B05C 1/00; B05C 1/06
(52) U.S. Cl. ........................ 118/215; 118/256; 118/56; 118/105; 427/230
(58) Field of Search ................................. 118/254, 205, 118/214, 215, 256, 268, 56, 105; 427/230

(56) References Cited

U.S. PATENT DOCUMENTS 3,335,700 A * 8/1967 Di Grado et al. ........... 118/215
3,850,532 A * 11/1974 Kaiser ........................ 401/219
6,123,478 A * 9/2000 Giles ......................... 401/219

\* cited by examiner

*Primary Examiner*—Richard Crispino
*Assistant Examiner*—Yewebdar T Tadesse
(74) *Attorney, Agent, or Firm*—Herbert Dubno; Andrew Wilford

(57) ABSTRACT

An inside wall of an elongated syringe body is coated by supplying at least an outer surface of an applicator ring with a coating of silicon oil while displacing a rod carrying the coated ring from a rear end to a front end of the body with the ring in continuous annular engagement with the inside wall thereof so as to transfer the oil from the ring to the inside wall. Thereafter a scraper ring also carried on the rod is displaced from the front end to the rear end of the body with the scraper ring in continuous annular engagement with the inside wall so as to scrape excess silicone oil from the inside wall.

5 Claims, 2 Drawing Sheets

COATING INSIDE OF SYRINGE

FIELD OF THE INVENTION

The present invention relates to an apparatus for coating a primary package. More particularly this invention concerns the coating of an inside wall of a syringe body.

BACKGROUND OF THE INVENTION

A standard disposable syringe comprises a tubularly cylindrical syringe body having a front end provided with a cannula or needle. The body is provided internally with a piston that defines with the front end a compartment that is filled with a medicament. A plunger connected to the piston can be pushed in to express the medicament from the body. The body is typically made of class 1 hydrolytic glass and the piston of a suitable elastomer.

It is important that the piston move easily in the body so that the medicament can be expressed smoothly or in small doses. Thus it is known to coat the inside surface of the syringe with a silicone oil.

The silicone-oil coating must be uniformly applied to the inner body wall and normally also to the outer surface of the piston. This coating must also be as thin as possible in order to avoid droplets from clogging the cannula.

OBJECTS OF THE INVENTION

It is therefore an object of the present invention to provide an improved apparatus for coating an inside surface of a syringe body or the like.

Another object is the provision of such an improved apparatus for coating an inside surface of a syringe body or the like which overcome the above-given disadvantages, that is which forms a very thin and uniform coating, and that are quite simple and inexpensive to use.

SUMMARY OF THE INVENTION

The coating apparatus according to the invention has an applicator ring having an outer surface and a system for supplying at least the outer surface of the applicator ring with a coating of silicon oil. This coated ring is displaced from a rear end to a front end of the body with the ring in continuous annular engagement with the inside wall thereof so as to transfer the oil from the ring to the inside wall. A scraper ring is then displaced from the front end to the rear end of the body with the scraper ring in continuous annular engagement with the inside wall so as to scrape excess silicone oil from the inside wall.

The rings are both mounted according to the invention n a rod formed with a passage opening at the applicator ring and connected to the silicone-oil supply. This rod is formed with respective radially outwardly open grooves carrying the rings and the rings are elastomeric O-rings. The passage opens into the groove of the applicator ring at a plurality of offset locations to ensure that the applicator ring is uniformly coated over its entire annular surface.

The groove of the scraper ring according to the invention has a width substantially greater than a diameter of the scraper ring and the rod is provided with a retaining washer received in the scraper-ring groove. The scraper ring lies between the washer and the applicator-ring groove.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
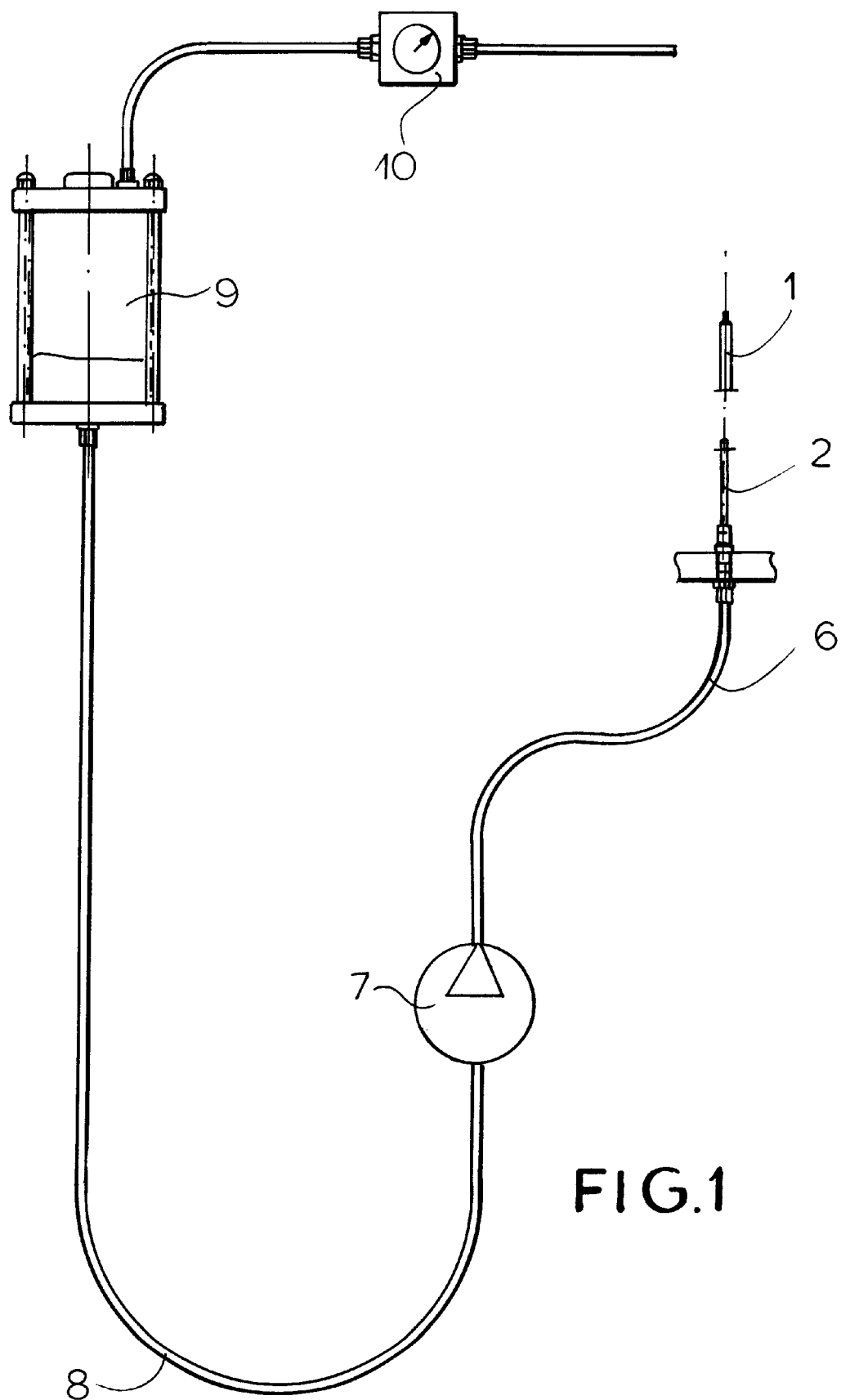
FIG. 1 is a largely diagrammatic view of the system of this invention before the start of a coating operation.
Figure 4:
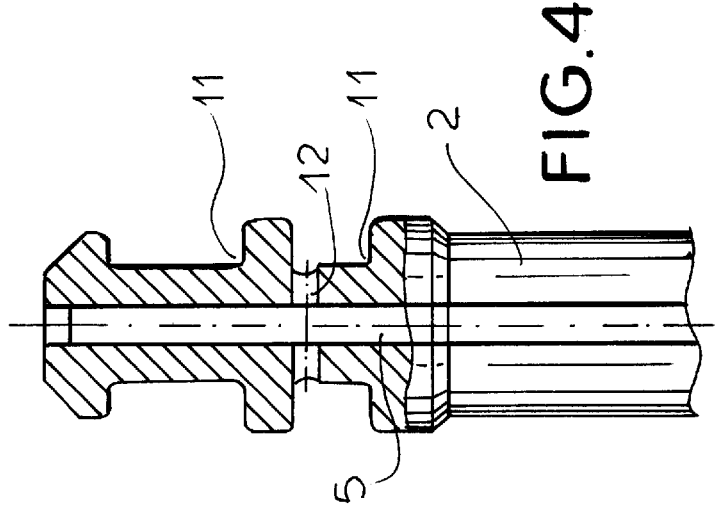
FIG. 4 is a partly sectional large-scale view of a detail of FIG. 3.
Figure 3:
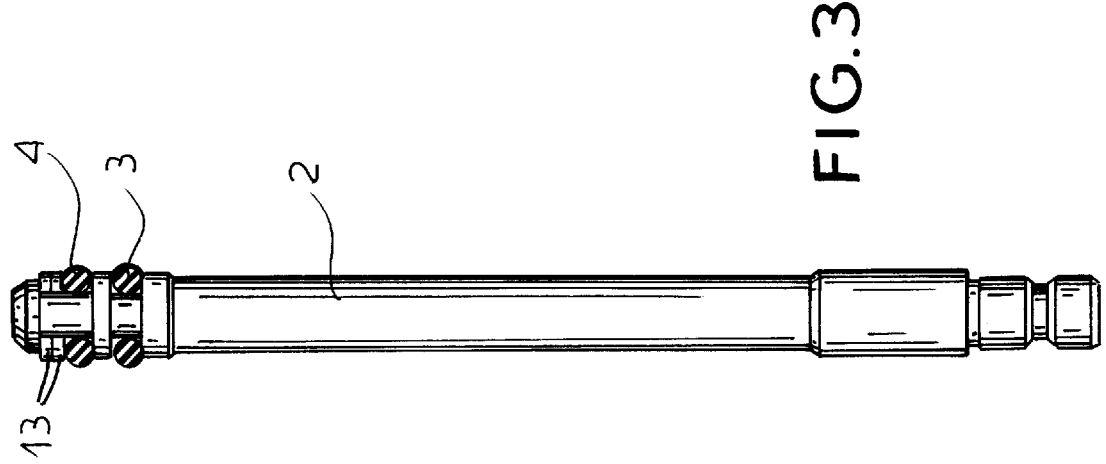
FIG. 3 is a large-scale view of the coating tool.
Figure 2:
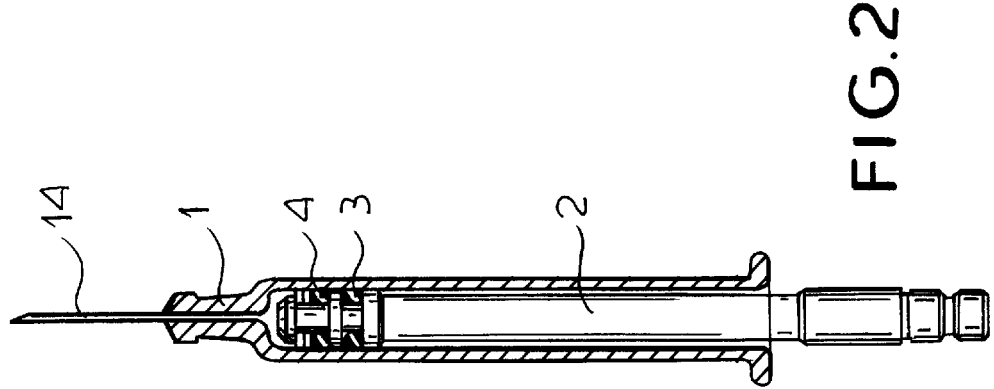
FIG. 2 is a large-scale sectional view of a detail of the system in the middle of the coating operation.

As seen in FIG. 1 a syringe 1 is internally coated by a coating tool or rod 2 having as shown in FIGS. 2 and 3 an applicator ring 3 and a doctor or scraper ring 4. Silicone oil is fed to the output of a pump 7 whose intake is connected through another tube 8 to a supply 9 of the oil which is pressurized by a valve 10.

More specifically, the rod 2 is formed with a pair of outwardly open square-section grooves 11 that receive O-rings forming the applicator ring 3 and scraper ring 4, the latter secured in place by retaining washers 13 having an outside diameter slightly smaller than the inside diameter of the tubular syringe body 1. Two or more radial bores 12 extend from the central feed passage 5 to the front end of the groove 11 for the applicator ring 3 so as to feed the oil to this groove 11 and ring 3 at several locations.

In use the rod 2, which is rigid and has an outside diameter substantially smaller than the inside diameter of the body 1, is inserted into the rear end of the cylindrical body 1 while the pump 7 is operating to feed a small amount of the oil from the supply 9 to the groove 11. This liquid coats the ring 3 as the rod 2 is pushed axially all the way into the body 1 until it is at its front end adjacent a needle 14 carried thereby. During this insertion the silicone oil is transferred to the inner surface of the body 1 in a fairly uniform and somewhat thick coating.

Then the rod 2 is retracted so that the front scraper ring 4 scrapes back over the surface, leaving behind a very thin coating about 2 μm thick. Thereafter a medicament is filled into the syringe body 1, an unillustrated piston and plunger are fitted into the syringe body 1, and the device is sterilized and packaged for sale.

I claim:

1. An apparatus for coating an inside wall of an elongated syringe body, the apparatus comprising:
    a rod fittable inside the syringe body and formed with a pair of radially outwardly open grooves and with a passage opening at one of the grooves;
    an applicator ring having an outer surface and set in the one groove;
    means connected to the passage for supplying at least the outer surface of the applicator ring with a coating of silicon oil;
    a scraper ring set in the other of the grooves; and
    means for displacing the rod and the coated ring from a rear end to a front end of the body with the ring in continuous annular engagement with the inside wall thereof so as to transfer the oil from the ring to the inside wall and for displacing the rod and the scraper ring from the front end to the rear end of the body with the scraper ring in continuous annular engagement with the inside wall so as to scrape excess silicone oil from the inside wall.

2. The syringe-body coating apparatus defined in claim 1 wherein the rings are O-rings.

3. The syringe-body coating apparatus defined in claim 1 wherein the passage opens at a plurality of offset locations into the applicator-ring groove.

4. The syringe-body coating apparatus defined in claim 1 wherein the groove of the scraper ring has a width substantially greater than a diameter of the scraper ring and the rod is provided with a retaining washer received in the scraper-ring groove, the scraper ring lying between the washer and the applicator-ring groove.

5. An apparatus for coating an inside wall of an elongated syringe body, the apparatus comprising:

- a rod formed with a pair of radially outwardly open grooves and with a passage opening at one of the grooves;
- an applicator ring having an outer surface and set in the one groove;
- means connected to the passage for supplying at least the outer surface of the applicator ring with a coating of silicon oil;
- a scraper ring set in the other of the grooves, the other groove having a width substantially greater than a diameter of the scraper ring;
- a retaining washer set in the other groove, the scraper ring lying between the retaining washer and the applicator-ring groove; and
- means for displacing the rod and the coated ring from a rear end to a front end of the body with the ring in continuous annular engagement with the inside wall thereof so as to transfer the oil from the ring to the inside wall and for displacing the rod and the scraper ring from the front end to the rear end of the body with the scraper ring in continuous annular engagement with the inside wall so as to scrape excess silicone oil from the inside wall.

* * * * *